United States Patent
Jenks et al.

(10) Patent No.: US 8,112,869 B2
(45) Date of Patent: Feb. 14, 2012

(54) AVASCULAR NECROSIS CAGE MANUFACTURING PROCESS

(75) Inventors: Philip J. Jenks, Warsaw, IN (US); Jon M. Heckman, Warsaw, IN (US); Mylin L. Cumberland, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 539 days.

(21) Appl. No.: 12/337,978

(22) Filed: Dec. 18, 2008

(65) Prior Publication Data

US 2010/0161063 A1  Jun. 24, 2010

(51) Int. Cl.
*B23P 11/00* (2006.01)
(52) U.S. Cl. .............. 29/525.01; 29/527.1; 623/18.11
(58) Field of Classification Search .............. 29/447, 29/527.1, 527.2, 525.01; 72/413, 415
See application file for complete search history.

(56) References Cited

U.S. PATENT DOCUMENTS

| | | | |
|---|---|---|---|
| 4,820,305 A | 4/1989 | Harms et al. | |
| 5,609,637 A | 3/1997 | Biedermann et al. | |
| 6,447,531 B1 * | 9/2002 | Amplatz | 606/200 |
| 6,511,748 B1 | 1/2003 | Barrows | |
| 2002/0123750 A1 | 9/2002 | Eisermann et al. | |

FOREIGN PATENT DOCUMENTS

| WO | WO 96/01599 | 1/1996 |
|---|---|---|
| WO | WO 2005/102224 | 11/2005 |
| WO | WO 2006/116761 | 11/2006 |

OTHER PUBLICATIONS

Depuy Acromed, Surgical Titanium Mesh, Product Catalog, TM01-10-000 Nov. 1999, 1999, 20 Pages.
European Search Report From Corresponding EPO Application No. 09178125.2-2310, Dated Mar. 5, 2010, 5 Pages.

* cited by examiner

*Primary Examiner* — David Bryant
*Assistant Examiner* — Moshe Wilensky

(57) ABSTRACT

A method for manufacturing a spherical cage. The method includes providing a wire braid and inserting a spherical ball inside the wire braid. The wire braid and spherical ball are placed inside a mold. Excess wire braid is trimmed from the mold, creating trimmed ends of the braid. The mold is heat set with the spherical ball and wire braid. The spherical ball and wire braid are removed from the ball and the spherical ball is removed from the wire braid, resulting in a spherical wire cage.

17 Claims, 7 Drawing Sheets

AVASCULAR NECROSIS CAGE MANUFACTURING PROCESS

TECHNICAL FIELD OF THE INVENTION

The present invention relates generally to the field of orthopedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

One type of bone damaging disease is Avascular Necrosis (AVN). In AVN, the bone is damaged due to a loss of blood supply. Eventually, the bone tissue dies, causing the bone to collapse. In a hip joint, AVN can cause the collapse of the femoral head.

Most commonly, AVN is treated by an orthopedic surgeon who performs a total hip replacement (THR) procedure. In a THR procedure, the entire hip joint is replaced with a prosthetic implant. The implant includes an acetabular cup that fits in the acetabulum, a ball for mating with the acetabular cup, and a stem that extends into the femur. However, this is a very invasive and major surgery.

In China, at least one surgeon has used a spherical Nickel Titanium alloy, more commonly known as Nitinol cage. A canal is drilled through the femur and the Nitinol cage is inserted. The Nitinol cage is compressed during insertion and placed inside of the femoral head. Once inside the femoral head, the Nitinol cage then returns to its spherical shape and reinforces the femoral head. The canal is then packed full of bone graft or bone cement.

However, there are problems in manufacturing the cages. In China, the cages were hand made. Utilizing hand made cages is prohibitive to mass manufacture and use. Others have tried to consistently mass manufacture Nitinol cages using mechanical methods without any success, creating a Nitinol tube, and not a sphere as needed.

The present invention is directed to alleviate at least some of the problems with the prior art.

SUMMARY OF THE INVENTION

According to one embodiment of the present invention, a method for manufacturing a spherical cage is provided. The method includes providing a wire braid and inserting a spherical ball inside the wire braid. The wire braid and spherical ball are placed inside a mold. Excess wire braid is trimmed from the mold, creating trimmed ends of the braid. The mold is heat set and the spherical ball and wire braid are removed from the mold. The spherical ball is removed from the wire braid, resulting in a spherical wire cage.

According to another embodiment of the present invention, a spherical cage is made by the process described above.

According to yet another embodiment of the present invention, a method for manufacturing a spherical cage made of Nitinol wire is provided. The method includes providing a cylindrical Nitinol braid made of the Nitinol wire. A spherical ball is placed in the cylindrical braid and the braid and ball are placed in a mold having a top half and a bottom half. The braid that extends out from the mold is trimmed. The mold is clamped and is then heat set.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
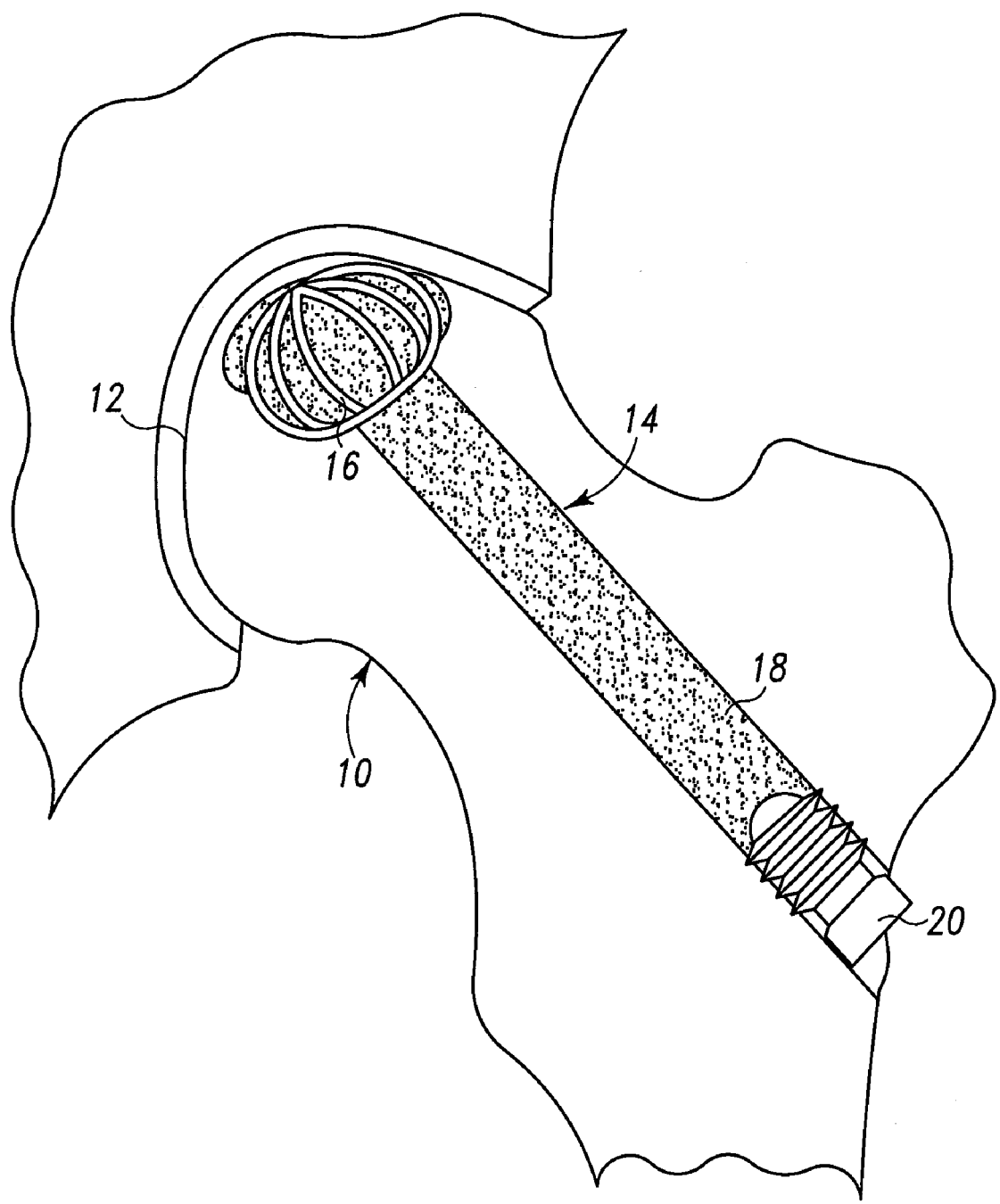
FIG. 1 is a perspective view of a Nitinol cage inside of a femoral head.

Referring first to FIG. 1, a femur 10 is illustrated. The femur 10 includes a head 12 that is damaged by AVN. In order to repair the damaged head 12, a canal 14 is drilled through the femur 10 and head 12. A cage 16 is inserted through the canal 14, and provides support to the damaged head 12. Tampered bone graft 18 is used to fill in the canal 14 and any voids. A screw 20 may also be used to further plug the canal 14. The cage 16 is made of Nitinol, a biocompatible material that is able to be compressed during insertion through the canal and then will regain its shape. Other biocompatible materials that are compressible and that can return to their original shape after being compressed may also be used.

Figure 2:
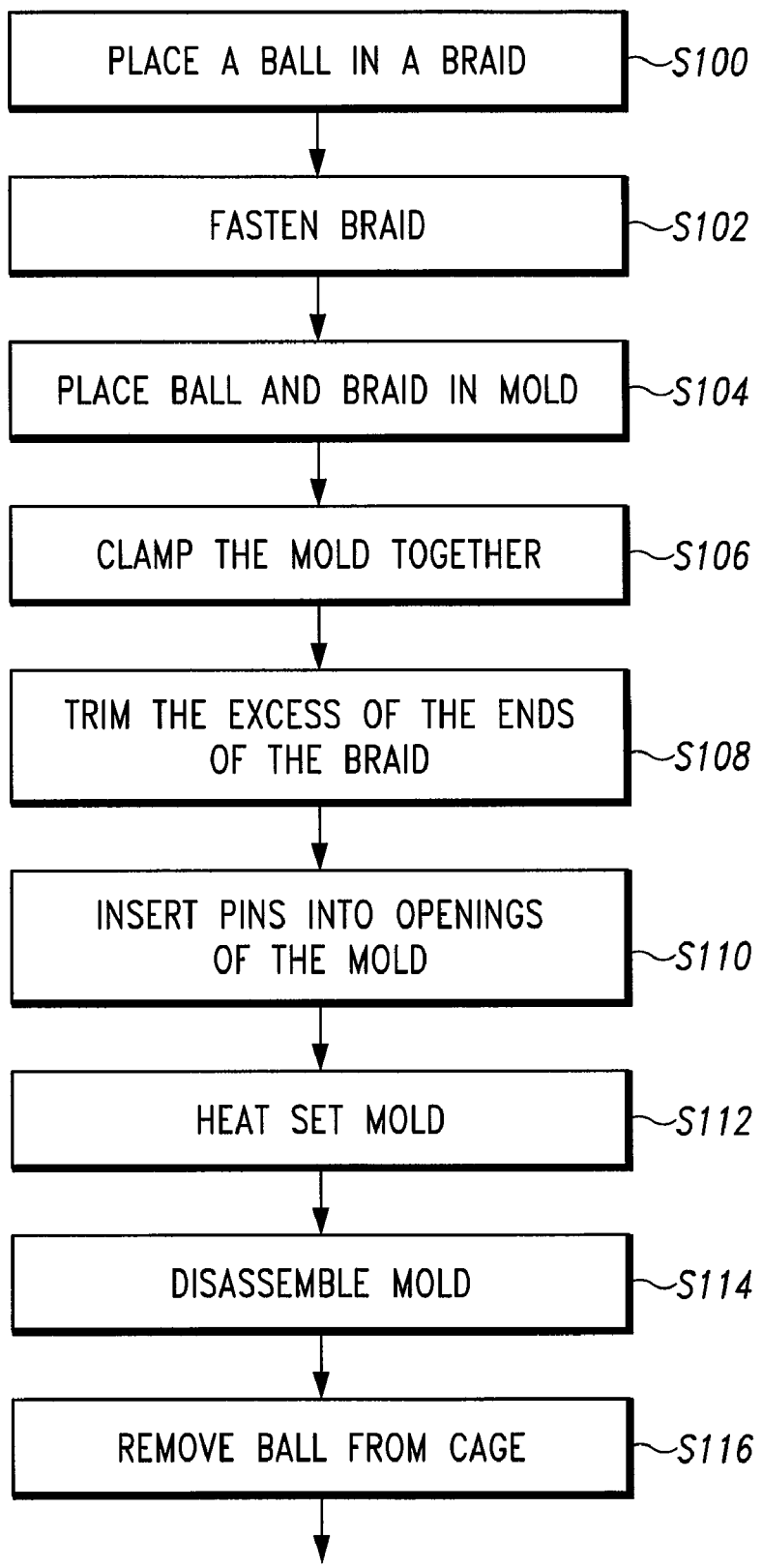
FIG. 2 is a flow chart of a method for fabricating a Nitinol cage according to one embodiment of the present invention.
Figure 3:
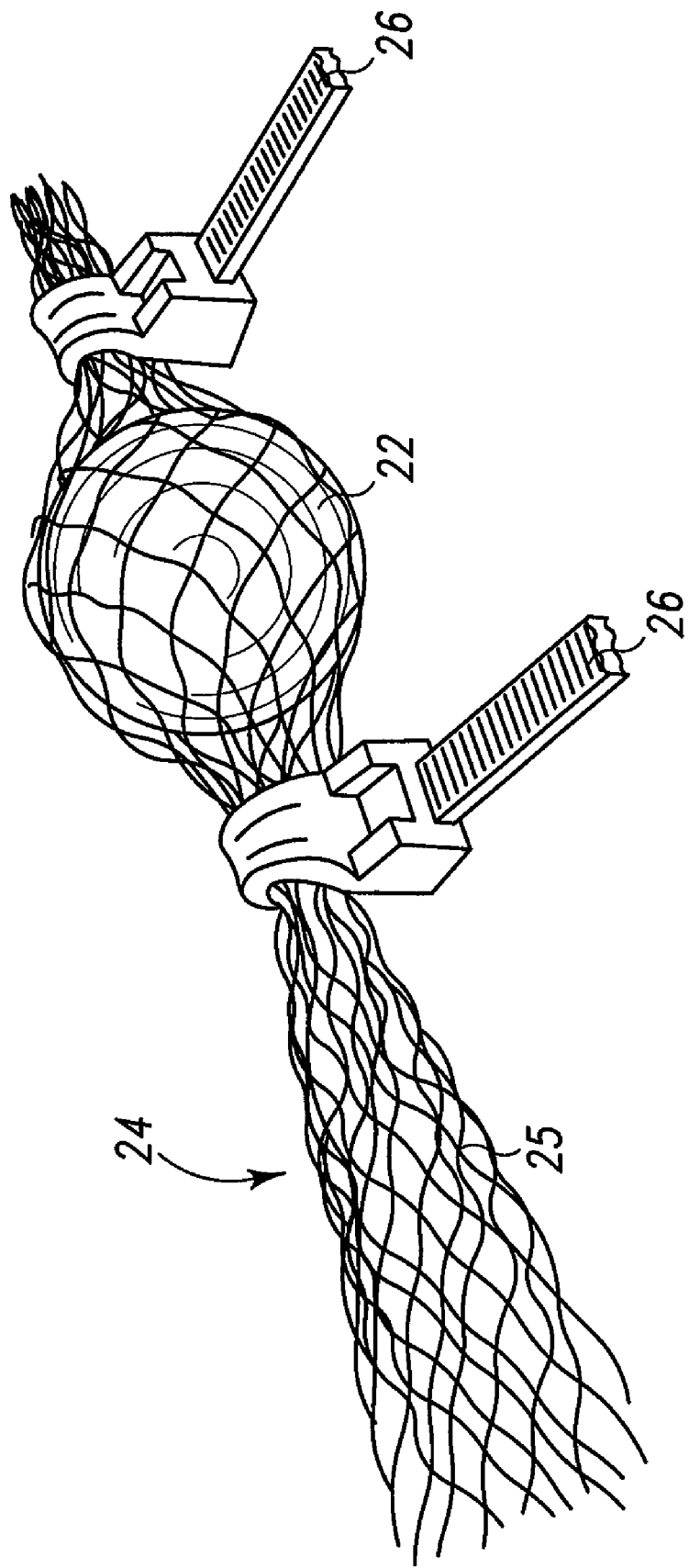
FIG. 3 is a perspective view of a ball in Nitinol braid to illustrate a step in the manufacturing process of FIG. 2.

Turning now to FIG. 2, a method for manufacturing the cage 16 will be described. First, at step s100, a spherical ball 22 is placed into a braid 24 made of wire 25 (FIG. 3). The braid 24 is used to form the final cylindrical cage 16. In the illustrated embodiment, the braid is made of Nitinol, although as discussed above the cage may be made of other materials. Nitinol braids are commonly manufactured items often used in stents or cardiac applications. The spherical ball 22 is selected based on what size the resulting cage should be. The spherical ball 22 may be a spherical steel gage ball. In other embodiments, the ball 22 may be made of other metals or ceramics. In some embodiments, the spherical ball 22 is selected from a plurality of spherical balls having a diameter ranging from about 20 mm to about 30 mm. In some embodiment, the diameters of the plurality of spherical balls are 20 mm, 25 mm, and 30 mm.

Returning now to FIG. 2, at step s102, the braid 24 is then fastened by a pair of mechanical fasteners 26 (FIG. 3). The mechanical fasteners may be ties, clamps, or other known fastening methods. In other embodiments, the braid 24 may not be clamped at all.

Figure 4:
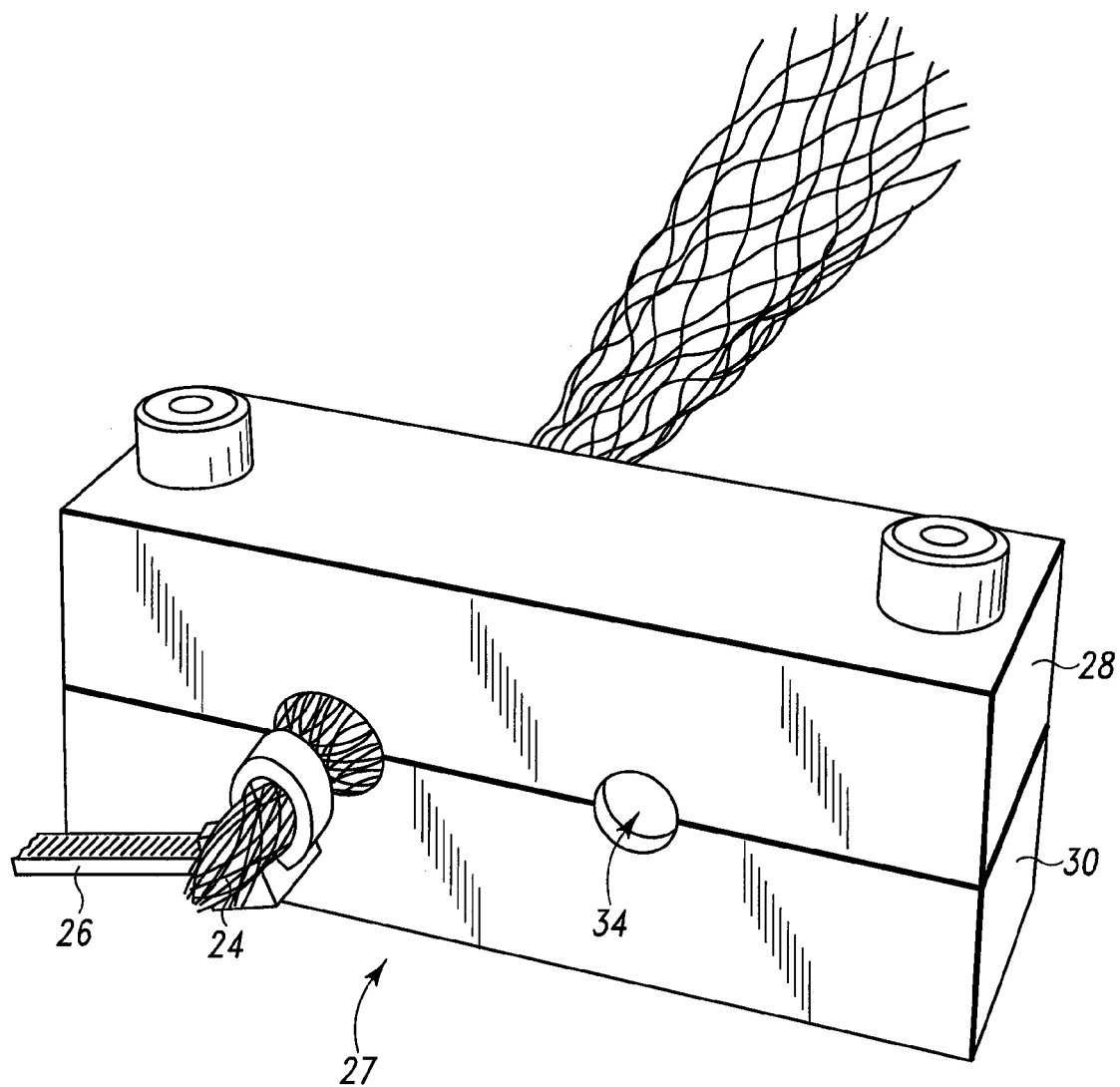
FIG. 4 is a perspective view of another step in the manufacturing process of FIG. 2.
Figure 6:
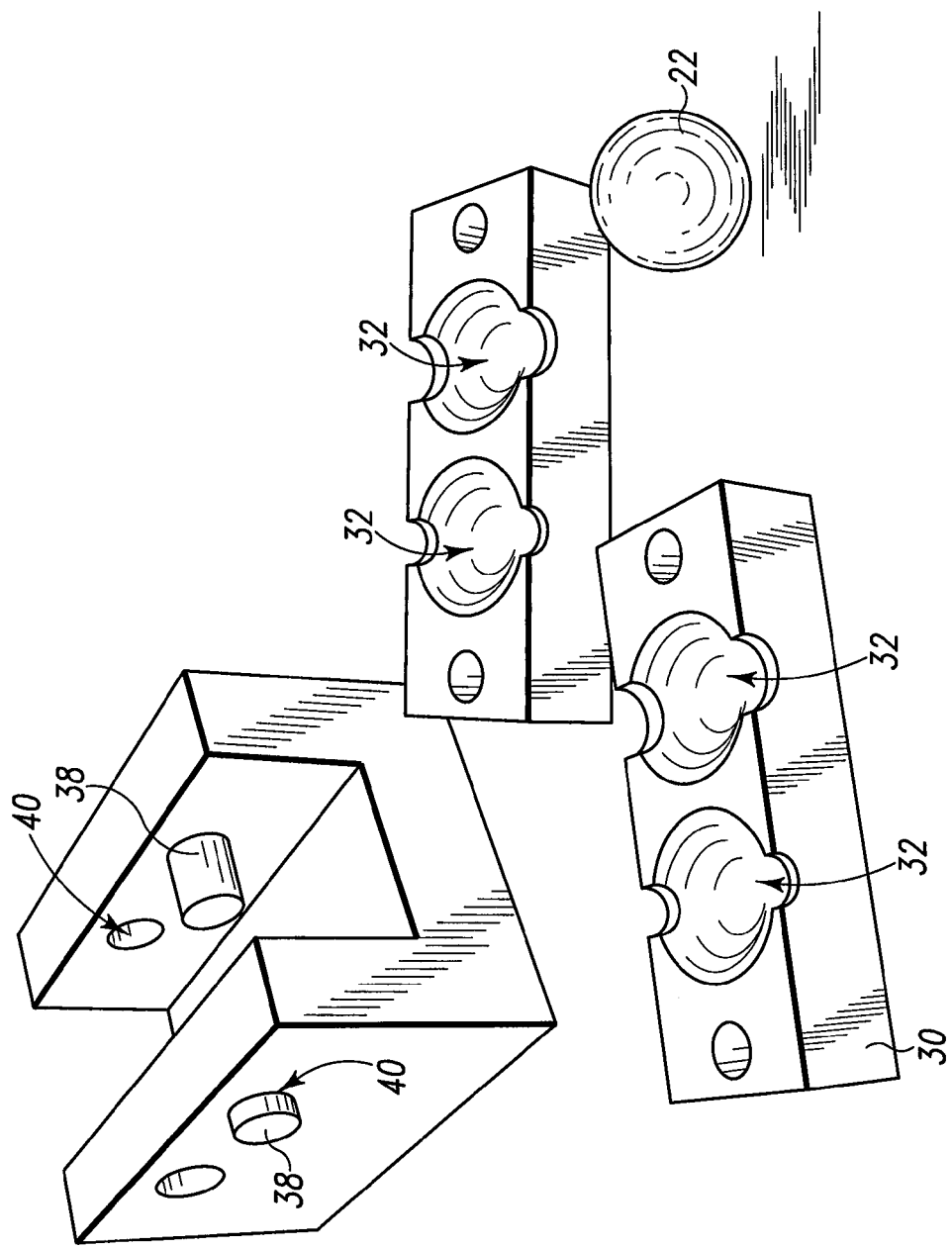
FIG. 6 is a disassembled view of a mold, illustrating pins that are inserted in the manufacturing process of FIG. 2.

At step s104, the braid 24 and ball 22 are placed into a mold 27 (FIG. 4). The mold 27 may be made of stainless steel, other metal, or ceramic. The mold 27 includes a top half 28 and a bottom half 30. Each of the top half 28 and the bottom half 30 include a hemispherical cavity 32 that has a diameter larger than the diameter of the spherical ball 22 (FIG. 6). In some embodiments, the diameter of the hemispherical cavity is equal to the diameter of the spherical ball 22 plus four times the diameter of the wire 25. In some embodiments, the mold 27 may have more than one cavity 32 as shown in FIG. 6. If the mold 27 has a plurality of cavities 32, the cavities 32 may be of the same size to enable the manufacture of more than one cage 16 using one mold 27. Alternatively, the cavities 32 may be of differing sizes, allowing the same mold 27 to be used to make different size cages 16.

As shown in FIG. 4, the ball 22 and braid 24 are placed in the cavity 32 of the bottom half 30 of the mold 27. The top half 28 of the mold 27 is then placed on top of the bottom half 30 such that the hemispherical cavities 32 are aligned, creating a spherical cavity. The mold 27 also includes side openings 34. The side openings 34 allow for the fasteners 26 and excess braid 24 to extend out from the mold 27.

Figure 5:
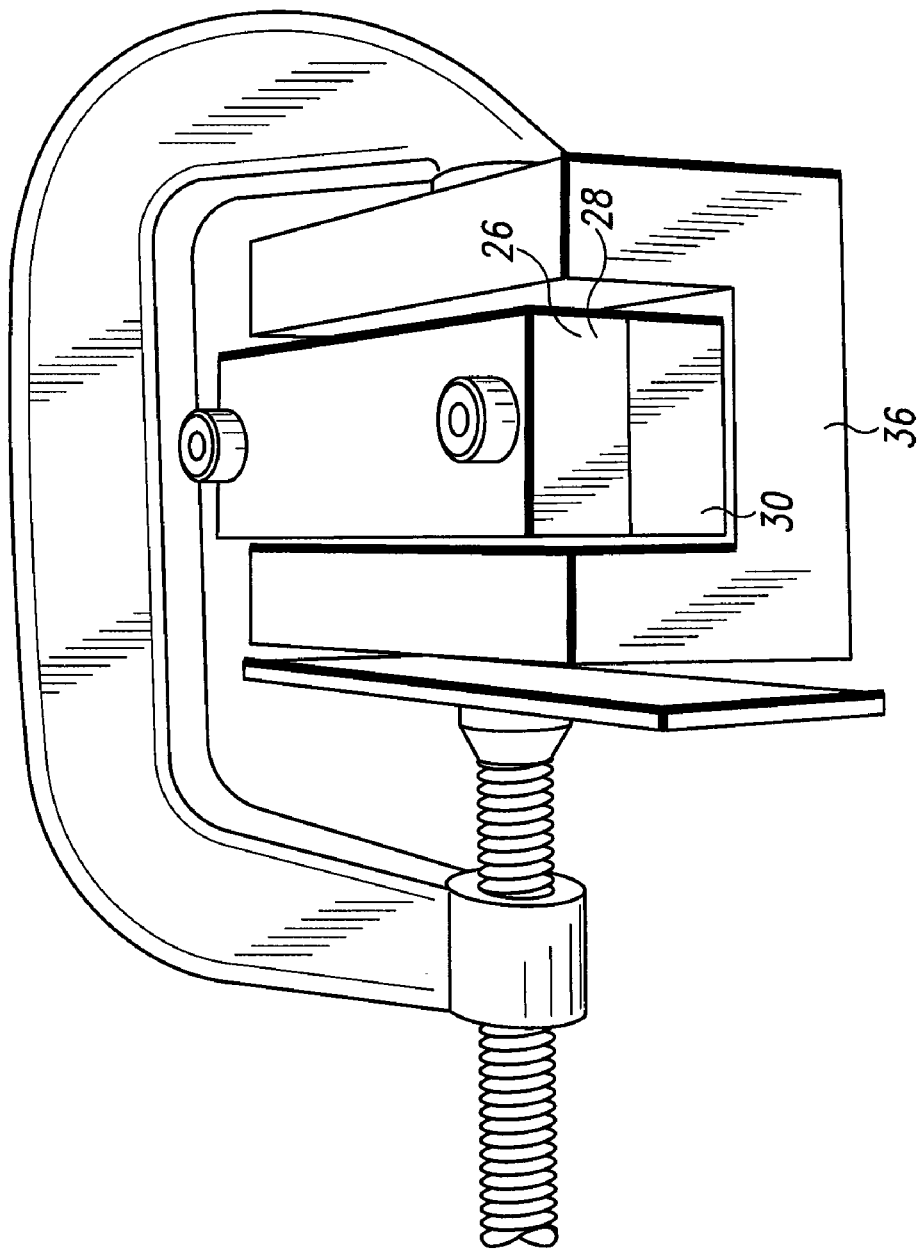
FIG. 5 is a perspective view of a clamping step in the manufacturing process of FIG. 2.

Returning to FIG. 2, at step s106, the top half 28 and bottom half 30 of the mold 27 are placed into a cradle 36 and clamped together (FIG. 5). The clamping force further presses the braid 24 into a spherical shape. At step s108, the excess braid 24 is trimmed as close to the ball as possible.

At step s110, two pins 38 (FIG. 6) are urged through side openings 40 on the cradle 36 and side openings 34 on the mold 27. The side openings 40 correspond with the side openings 34 of the mold 27 in order for the pins 38 to be urged through both sets of side openings 34, 40. The pins 38 force the trimmed ends of the braid 24 to conform to the spherical shape of the ball 22. Preferably, the two pins have the same spherical form at the end that is inserted into the side openings 34, 40, to ensure that the trimmed ends of the braid 24 are similarly shaped. In other embodiments, differently shaped ends may be used. The pins 38 may be made of stainless steel. Alternatively, the pins 38 may be made of other metals.

At step s112, the mold 27, along with the ball 22 and braid 24, are inserted into an oven and heat set. In one embodiment, the oven is set at 525° C. The mold, cage and ball were then heated for a period of three to four hours. In other embodiments, other known heat setting temperatures and times may be used.

Figure 8:
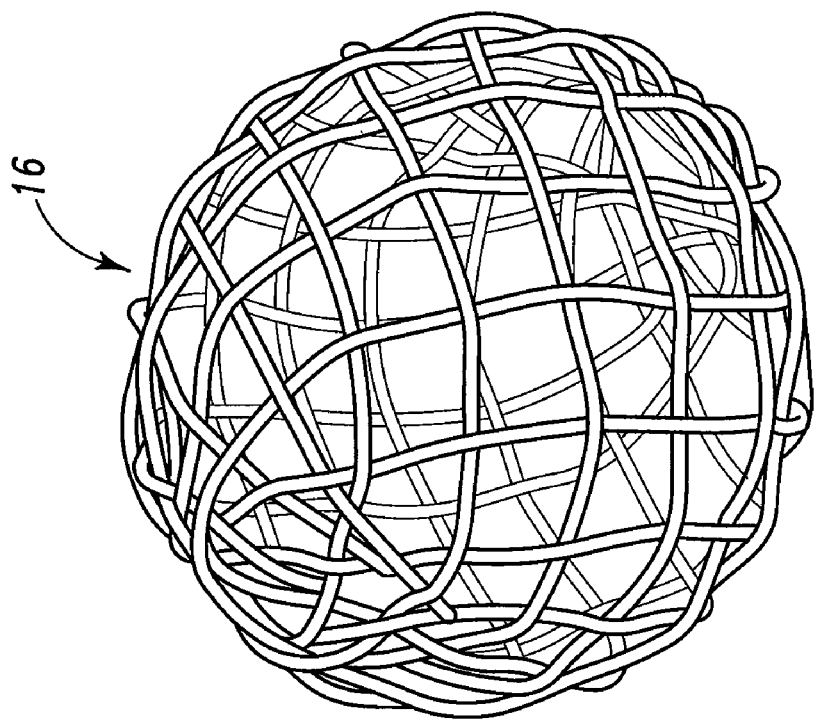
FIG. 8 is a perspective view of the final cage after the manufacturing process of FIG. 2 is completed.
Figure 7:
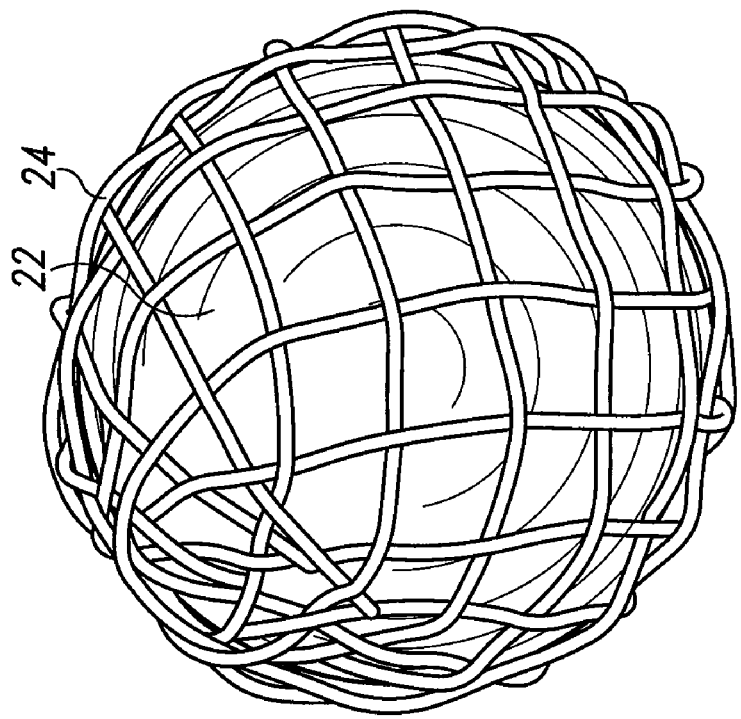
FIG. 7 is a perspective view of the ball and cage during the manufacturing process of FIG. 2.

After heat setting, at step s114, the mold is dissembled and the ball 22 and braid 24 are removed (FIG. 7). Next, at step s116, the ball 22 is removed from the now spherical braid, resulting in the spherical cage 16 shown in FIG. 8. The ball 22 is squeezed out through the cage 16. Because of Nitinol's shape-memory properties, the cage 16 springs back into its spherical shape.

Although the present invention and its advantages have been described in detail, it should be understood that various changes, substitutions, and alterations can be made therein without departing from the spirit and scope of the present invention as defined by the appended claims.

The invention claimed is:

1. A method for manufacturing a spherical cage, the method comprising:
   providing a wire braid;
   inserting a spherical ball inside the wire braid;
   placing the wire braid and spherical ball inside a mold, which has a pair of openings, one on each of two opposite sides of the mold so that, once the wire braid and the spherical ball are placed inside the mold, the excess wire of the braid on one side of the spherical ball protrudes from one of the openings and the excess wire of the braid on the opposite side of the spherical ball protrudes from the other of the openings;
   trimming excess wire braid from the mold which extends through the openings beyond the mold, creating trimmed ends of the braid;
   forcing the trimmed ends of the braid into the openings in the mold so the trimmed ends are forced to conform to the shape of the spherical ball;
   heat setting the mold with the spherical ball and wire braid;
   removing the spherical ball and wire braid from the mold; and
   removing the spherical ball from the wire braid, resulting in a spherical wire cage.

2. The method of claim 1, further comprising applying fasteners to either side of the wire braid after the spherical ball has been placed inside the wire braid.

3. The method of claim 1, wherein the forcing is done by placing two steel pins through the openings.

4. The method of claim 1, wherein removing the spherical ball from the braid comprises squeezing the ball out of the braid.

5. The method of claim 1, wherein the wire braid is made of a biocompatible metal.

6. The method of claim 5, wherein the biocompatible metal is Nitinol.

7. The method of claim 1, wherein the spherical ball is a metal ball or a ceramic ball.

8. The method of claim 7, wherein the spherical ball is a stainless steel gage ball.

9. The method of claim 1, further comprising selecting the spherical ball from a plurality of spherical balls having different diameters.

10. A spherical wire cage made by the process of claim 1.

11. A method for manufacturing a spherical cage made of Nitinol wire, the method comprising:
    providing a cylindrical Nitinol braid made of the Nitinol wire;
    placing a spherical ball in the cylindrical braid;
    fastening the braid on both sides of the spherical ball;
    placing the spherical ball and the braid in a mold having a top half and a bottom half, when the top half and the bottom half are assembled, the assembled halves have a pair of openings, one on each of two opposite sides of the mold so that, once the wire braid and the spherical ball are placed inside the mold, the excess wire of the braid on one side of the spherical ball protrudes from one of the openings and the excess wire of the braid on the opposite side of the spherical ball protrudes from the other of the openings;
    trimming the braid that extends out from the openings in the mold, creating trimmed ends;
    forcing the trimmed ends of the braid into the openings in the mold so the trimmed ends are forced to conform to the shape of the spherical ball clamping the mold; and
    heat setting the mold.

12. The method of claim 11, further comprising removing the ball and braid from the mold after heat setting.

13. The method of claim 12, further comprising removing the ball from the braid, leaving a spherical wire cage.

14. The method of claim 11, where the fastening is done using ties.

15. The method of claim 11, further comprising selecting a spherical ball from a plurality of spherical balls, each of the plurality of spherical balls having a different radius.

16. The method of claim 11, wherein the top half and bottom half of the molds each have a hemispherical cavity and that the hemispherical cavities of the top half and bottom half of the molds have a diameter that is greater than the diameter of the ball.

17. The method of claim 16, wherein the diameter of the hemispherical cavities is equal to the diameter of the spherical ball plus four times the diameter of the Nitinol wire.

* * * * *